(12) United States Patent
Brown

(10) Patent No.: US 9,315,804 B2
(45) Date of Patent: Apr. 19, 2016

(54) METHOD OF SELECTING APTAMERS

(75) Inventor: Clive Gavin Brown, Cambourne (GB)

(73) Assignee: Caris Life Sciences Switzerland Holdings, GmbH, Basel (CH)

(*) Notice: Subject to any disclaimer, the term of this patent is extended or adjusted under 35 U.S.C. 154(b) by 1119 days.

(21) Appl. No.: 12/739,087

(22) PCT Filed: Oct. 22, 2008

(86) PCT No.: PCT/GB2008/003581
§ 371 (c)(1),
(2), (4) Date: Apr. 21, 2010

(87) PCT Pub. No.: WO2009/053691
PCT Pub. Date: Apr. 30, 2009

(65) Prior Publication Data
US 2010/0304991 A1   Dec. 2, 2010

(30) Foreign Application Priority Data

Oct. 22, 2007   (EP) .................................... 07020629

(51) Int. Cl.
*C12N 15/115*   (2010.01)
*C12N 15/10*   (2006.01)
*C12Q 1/68*   (2006.01)

(52) U.S. Cl.
CPC .......... *C12N 15/1048* (2013.01); *C12Q 1/6811* (2013.01)

(58) Field of Classification Search
None
See application file for complete search history.

(56) References Cited

U.S. PATENT DOCUMENTS 6,376,190 B1 *   4/2002   Gold et al. .................... 536/23.1
2008/0242560 A1 *   10/2008   Gunderson et al. ............. 506/26

FOREIGN PATENT DOCUMENTS

| EP | 1386 972 A1 | 2/2004 |
| EP | 2209914 B1 | 3/2014 |
| JP | 2002-534985 | 7/2001 |
| WO | WO 91/19813 A1 | 12/1991 |
| WO | WO 98/08856 A2 | 3/1998 |
| WO | WO 0043534 | 7/2000 |

OTHER PUBLICATIONS

Davis et al (2002 PNAS 99:11616-11621).*
Roulet et al (2002 Nature Biotechnology 20:831-5).*
Daniels et al (2002 Analytical Chemistry 305:214-26).*
S. Shamah, et al., "Complex Target SELEX," Accounts of chemical research, XP007906883, Jan. 2008, pp. 130-138, vol. 41, No. 1.
B. Vant-Hull, "Theoretical Principles of In Vitro Selection Using Combinatorial Nucleic Acid Libraries," XP009111025, Combinatorial Methods in Vucleic Acid Chemistry, Current Protocols in Nucleic Acid Chemistry, pp. 9.1.1-9.1.16, Unit 9.1.
K. Ikebukuro, et al., "Analysis of the evolution of the thrombin-inhibiting DNA aptamers using a genetic algorithm," Biotechnol. Lett., 2006, pp. 1933-1937, vol. 28.
H. Levine, et al., "A mathematical analysis of SELEX," Computational Biology and Chemistry, 2007, pp. 11-35, vol. 35.
T. Noma, et al., "Aptamer selection based on inhibitory activity using an evolution-mimicking algorithm," Biochemical and Biophysical Research Communications, 2006, pp. 226-231, vol. 347.
Bittker Ja et al.: "Nucleic acid Evolution and Minimization by Nonhomologous Random Recombination," Nature Biotechnology, vol. 20, Oct. 2002, pp. 1024-1029.
Kun A et al.: "Fitness Landscapes, Error thresholds, and Cofactors in Aptamer Evolution" in "The Aptamer Handbook", Klussmann S (ed.), Wiley-VCH 2006, pp. 54-85.
Nimjee Am et al.: "Aptamers to Proteins" in "The Aptamer Handbook", Klussmann S (ed.), Wiley-VCH 2006, pp. 131-163.
Notice of Allowance dated Nov. 14, 2014 for Chinese application No. 201110137477.0 (translation at pp. 4-5).
Office action dated Sep. 30, 2014 for Japanese application No. 2010530541 (translation at pp. 5-8).
Opposition dated Dec. 12, 2014 for European patent No. EP2209914.
Schuster P "Mathematical Models on RNA Evolution, Simulations In Silica, and Concepts for In vitro Selection" in "The Aptamer Handbook", Klussmann S (ed.), Wiley-VCH 2006, pp. 29-53.

* cited by examiner

*Primary Examiner* — Christopher M Gross
(74) *Attorney, Agent, or Firm* — Ramin Akhavan

(57) ABSTRACT

The present invention is a method for the identification of one or more aptamers to at least one target molecule, the method comprising: selecting candidate aptamer sequences that bind to a target molecule, assigning to the bound sequences a measure (fitness function) of each sequence's aptameric potential, allowing evolution of some or all of the sequences to create a new mixture of candidate sequences, and repeating the method with the newly created candidate aptamer pool until the aggregate aptameric potential of the candidate pool reaches a plateau, wherein sequences present in the final pool are optimal aptamers to the target molecule.

29 Claims, No Drawings

METHOD OF SELECTING APTAMERS

The present invention relates to the field of aptamers. In particular, the invention relates to a method of generating aptamer libraries and protein-specific aptamers for use in proteomics, such as protein biomarker identification.

Aptamers are short polymers, usually nucleic acids (DNA, RNA, PNA), that form well-defined three dimensional shapes, allowing them to bind target molecules in a manner that is conceptually similar to antibodies. Aptamers combine the optimal characteristics of small molecules and antibodies, including high specificity and affinity, chemical stability, low immunogenicity, and the ability to target protein-protein interactions. In addition to high specificity, aptamers have very high affinities to their targets. Typically, aptamers generated against proteins have affinities in the picomolar to low nanomolar range. In contrast to monoclonal antibodies, aptamers are chemically synthesised, rather than biologically expressed, offering a significant cost advantage (8,9).

Aptamers are typically produced through an in vitro evolutionary process called "Systematic Evolution of Ligands by EXponential enrichment" (SELEX) which is described in U.S. application Ser. No. 07/536,428, U.S. Pat. No. 5,475,096, and U.S. Pat. No. 5,270,163. The SELEX process involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX process includes steps of contacting the mixture with the target under conditions favourable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying, through as many cycles as desired, to obtain only sequences with highest binding affinities against the target molecule. Candidate oligonucleotides may include fixed or known motifs within the sequence. If purely random sequences were used, the finding of selective aptamers within a candidate population would rely entirely on chance. Indeed, the more random an oligonucleotide sequence, the more chance must be relied on for that sequence to be selective for the target under investigation (11, 12, 13).

In its most basic form, the SELEX process may be defined by the following series of steps:

1) A candidate mixture of nucleic acids of differing sequences is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomised sequences can be totally randomised (i.e., the probability of finding a base at any position being one in four) or only partially randomised (e.g., the probability of finding a base at any location can be selected at any level between 0 and 100 percent).

2) The candidate mixture is contacted with the selected target under conditions favourable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5-50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer weakly binding sequences and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule (11, 13).

One of the major problems when creating aptamer libraries is the sheer size of the possible search space. For example, there may be hundreds or thousands of possible oligonucleotide sequences that may be selective and specific for a single protein, but where does one start to find the best sequence?

The term 'search space' encompasses all possible or allowed variations of polymeric units, such as nucleotides, that can occur in an aptamer molecule of a given length. Because only a limited number of sequences can be interrogated at any one time, the candidate library can sample only a fraction of the possible search space of possible nucleotide sequences of a given length. For example, there are $10^{24}$ possible 40mers comprising four basic units (nucleotides for DNA/RNA). Thus, the aptamer search space (for 40mer nucleic acids) to typical protein space from a biological sample, assuming this comprises tens of thousands of different proteins, exists in a ratio of aptamer candidate polymers to proteins of $\sim 10^{20}$:1 (+/−a factor of 10). For 60mers it is $10^{32}$:1. Even if only 1 in $10^{10}$ sequences is strongly aptameric, this still leaves $10^{22}$:1 aptamers to proteins to be interrogated in order to find one strongly aptameric sequence.

However, it is likely that there are a large number of aptamers, of varying quality, for any given protein. SELEX therefore relies on the chance that a suitable sequence is present in an initial candidate mixture under test. The method then converges exponentially on the best solution available in the chosen mixture. Some prior knowledge of potentially suitable sequences, for example sequences that confer a particular 2D or 3D structure to the sequence, can be exploited during the candidate library design to ensure that the process is not entirely dictated by chance. Even so, the solution provided by SELEX is highly unlikely to provide the best solution for the problem, i.e. the best aptamer for a particular protein.

Thus, the SELEX process favours use of a single expressed and isolated protein target that is amenable to binding selection and proceeds blindly through rounds of amplification towards convergence on a small aptamer set or a single aptamer. The process finds the 'best' aptamer to the isolated protein from a set of given sequences by exponential and iterative selection. In the current published schemes, often only $1\times10^{-20th}$ of the potential sequence search space is utilised (8), although it is understood that certain basic sequence motifs have much more potential as aptamers than others. Nonetheless, it is unlikely that a current aptamer search finds the globally best fitting aptamer from the pool. Also, the outcome of the search is very dependant on the initial pool diversity. In most current SELEX schemes the aptamer must be in the initial search pool of candidate aptamers. It is also highly likely, given the small searches done to date, that each protein has a wide spectrum of possible aptamers within the full aptamer space. Because the SELEX scheme is exponential and, because the putative aptamer must generally be present in the initial library, SELEX will have difficulties selecting aptamers to multiple protein targets simultaneously, or to one protein target masked in a background of others. SELEX also cannot screen the full $10^{15}$ candidate aptamer sequences currently claimed as typical in literature. This is because library synthesis, typically on a commodity DNA/RNA synthesiser, cannot be quality controlled to the levels required to verify the library diversity. It is also highly likely that some of the aptamers in the library anneal (stick) to others, some will be stoichiometrically under-represented in the population because of biases in the synthesis process. Many aptamers will fold into a distribution of tertiary structure, some active, others not. Many will simply never have an opportunity to bind to the target protein because of their relative dilutions. Hence it is unlikely that $10^{15}$ candidate aptamers are actually screened against the protein and so the search is even more limited than believed and is dependent programming of the instrument generating the random sequences. Some variations on the SELEX scheme have been described in an attempt to circumvent these limitations by introducing random variability into the evolving aptamers (7).

Looked at in another way, SELEX is essentially a physical in vitro embodiment of a computational heuristic. An heuristic is an approximate method for helping to solve a problem where a 'good enough' answer is sufficient. In the present case, the problem is to find the best solution from a finite search space that is too large to search in toto. An heuristic is a computational method that uses trial and error methods to approximate a solution for computationally difficult problems. Put another way, an heuristic method or procedure is one which begins with only an approximate method of solving a problem within the context of some goal and then uses feedback from the effects of the solution to improve its own performance and thus move towards a better solution. SELEX implements a basic search of randomly generated candidate aptamer sequences against a target program, assesses the resulting success of each candidate sequence by virtue of its survival rate in the assay and then amplifies up the survivors before another round of reselection. Ultimately the strongest candidate sequences from the initial library, i.e. those that bind the target protein with the highest affinity, become progressively more enriched in the subsequent round of the procedure. The SELEX procedure is thus the implementation in the laboratory of a computational procedure to find the polymers (or nucleic acids) with the highest binding affinity to a protein under study. The SELEX procedure could be entirely and deterministically modelled in silico if all of the physicochemical properties of aptamers and proteins, and the causes of their behaviours, were known. The process can be approximated with less perfect knowledge (17). Further examples of the use of biomolecules to solve computational problems more explicitly have been published (1, 2, 3, 4, 5).

The inventors have appreciated that, to solve the present problem and improve on the search capacity and solution offered by SELEX, an intelligent method is needed to search the aptamer search space and find optimal solutions to deal with the scale of the problem presented by the large numbers of proteins present in the proteome and the extremely large number of possible candidate aptamers to each protein.

The evolutionary growth of populations of candidate solutions as a means for searching for answers to complex problems with a very large number of possible solutions has been well described computationally (14, 15, 16) and is best embodied in so-called Genetic Algorithms, a particular class of evolutionary search heuristics. Genetic Algorithms are search algorithms based on the mechanics of natural selection and natural genetics: reproduction, mutation, recombination, natural selection and survival of the fittest. They combine survival of the fittest among encoded representation of candidate solutions, for example string structures, with a structured yet randomised information exchange. This allows one to form a search algorithm with some of the innovative flair of human search. Candidate solutions to the optimisation problem under study play the role of artificial creatures (individuals) in a population. Evolution of the population then takes place after the repeated application of the above operators; mutation, cross-over reproduction and selection. In every generation, a new set of artificial creatures (strings or binary encodings) is created using bits and pieces of the fittest of the old or previous population. An occasional new part is tried for good measure. Genetic algorithms efficiently exploit historical information to speculate on new search points with expected improved performance (14).

In these schemes, a search problem is encoded, with each possible solution s being represented as a chain, sequence or string of numbers or letters. This encoding is for convenience of execution of the heuristic only. These chains, sequences or strings of numbers or letters are often described, by analogy, as a 'genome'. Each artificial individual solution thus has its own genome. While a large initial population of candidate solutions (genomes) is generated, the population represents only a very small proportion of the total number of possible candidate solutions that could be encoded exhaustively. These heuristics are typically deployed where an approximate answer is sought from a search space that is far too large to be tractable to exhaustive searching. A 'fitness function' or 'objective function' $f$ is applied to each possible solution s or member of the candidate population. This function is an assessment of the individual solution's closeness to the characteristics of the optimal solution. A high $f(s)$ implies that s is a good solution.

Usually, an initial population of randomly generated candidate solutions s comprise the first generation. The fitness function $f$ is applied to the candidate solutions and any subsequent offspring. In selection, parents for the next generation s' are chosen with a bias towards higher fitness. Only 'fit' individuals, as measured by the fitness function $f$ and the application of a cut-off (e.g. upper quartile), are chosen to go through to a second round of mutations (random changes to their genome) and cross over parts of their 'genome' with other high scoring individuals (recombination or reproduction). The methods employed to do this require the algorithmic change of units of their 'genome' from one possibility to another and the production of prefix and suffix combinations of genomes at random points between any two fit genomes. Thus, a second generation of children is generated in addition to the original parent solutions. Expressing this in more detail, the parents reproduce by copying with recombination and/or mutation. Reproduction is a process in which individual candidates or strings are copied according to their fitness function $f$. This means that candidates with a higher fitness value have a higher probability of contributing one or more offspring to the next generation and some of their internally coded characteristics will be transmitted to their offspring. This operator, $f$ is an artificial version of natural selection, a Darwinian survival of the fittest among candidates. Once a candidate has been selected for reproduction, an exact replica of the candidate is made. This candidate is then entered into a mating pool, a tentative new population, for further generic operator action.

Recombination acts on the two selected parents (candidates) and results in one or two children (new candidates). After reproduction, simple crossover may proceed in two steps. First, members of the new candidates or children in the mating pool are mated at random. Second, each pair of new candidates undergoes crossing over to create another two new candidates.

Mutation acts on one candidate and results in a new candidate. Mutation is needed because, even though reproduction and crossover effectively search and recombine extant notions, occasionally they may become over-zealous and lose some potentially useful genetic material. In artificial systems, the mutation operator protects against such an irrevocable loss. Thus, mutation is an insurance policy against premature loss of important notions.

In summary, these operators create the offspring (a set of new candidates) and yield a new set of diverse yet similar individual candidate solutions (or genomes) of some arbitrary population size. This new set is assessed for its fitness and the best solutions survive to reproduce and mutate again. These new candidates compete with old candidates for their place in the next generation (survival of the fittest). This proceeds until the aggregate fitness of the population reaches a stable plateau. Often this means there are several individuals that are reasonable solutions to the search and often they have some characteristics in common. Thus the population of candidate solutions, encoded as they are, can converge towards a set of solutions that satisfy the given 'fitness' criteria. The resulting population of individuals may have little in common compositionally with the initial population. The number of such iterations and number of considered possibilities required to reach stable and highly fit candidate solution population is relatively small and far smaller that an exhaustive search.

Thus, Genetic Algorithms allow iterative searching for a solution or set of solutions to a problem in a space that is too big to search all at one time. The problem to be solved is first encoded in a set of candidate solutions and a fitness function is applied to each possible solution. The best solutions may then be identified. The heuristic then generates a diverse but similar population of 'children' carrying over the characteristics of their parents. The fitness question is then re-applied and the process repeated. Thus, one starts with a random approximation of the solution(s) to the search and the algorithm allows movement of the population towards an optimal set of solutions, bearing in mind that the best solution(s) is/are dependent on the robustness of the fitness function. While there may be several equally good solutions to a given problem, a strength of Genetic Algorithms is that, under the right conditions, these algorithms tend to find some or all of these equally good solutions.

With this in mind, the present invention encompasses an improvement on SELEX. Expressed in another way, the invention relates to the application of computational heuristics to improve SELEX. To this end, the invention resides in a physical embodiment of a Genetic Algorithm. Indeed, in one aspect, the present invention resides in the use of a genetic algorithm paradigm to direct polymeric sequence evolution in the design of candidate aptamer sequences.

Viewed in another way, the present invention resides in a method for the identification of one or more aptamers to at least one target molecule, the method comprising SELEX and characterised in that the method further comprises using the fitness of a candidate aptamer sequence to direct evolution of that sequence towards a best fit sequence for the or each target molecule.

Specifically, the present invention resides in a method for the identification of one or more aptamers to at least one target molecule, the method comprising:
a) selecting candidate aptamer sequences that bind to a target molecule;
b) assigning to the bound sequences a measure (fitness function) of each sequence's aptameric potential;
c) allowing evolution, by random or directed changes to some or all of the sequences, to create a new mixture of candidate sequences; and
d) repeating the steps a) to c) with the newly created candidate aptamer pool until the aggregate aptameric potential of the candidate pool reaches a plateau, wherein sequences present in the final pool are optimal aptamers to the target molecule.

More specifically, the method comprises:
a) contacting a pool of candidate polymer sequences with at least one target molecule;
b) partitioning unbound sequences from those sequences that have bound specifically to target molecule(s);
c) dissociating the sequence-target complexes to obtain a ligand-enriched mixture of sequences;
d) assigning to each sequence obtained in step c) a measure (fitness function) of the sequence's aptameric potential;
e) using the measure of step d) to determine the aptameric potential of the ligand-enriched mixture;
f) allowing evolution of some or all of the sequences obtained in step c) using information obtained in step e) to create a new mixture of sequences; and
g) repeating the steps a) to f) with the newly created candidate aptamer pool until the aggregate aptameric potential of the candidate pool reaches a plateau, wherein sequences present in the final pool are optimal aptamers to the at least one target molecule.

Thus, the method of the invention allows the identification of selective aptamers, indeed substantially the best aptamer (s), for a target. Candidate polynucleotide sequences of the aptamers themselves represent possible solutions within a search space, the search space being all possible aptamers (and implicitly their sequences). The use of sequence evolution allows the population of possible solutions to move towards the optimum solution. Thus, sequences in the final pool need not and, indeed, are highly unlikely to have been present in the original search pool. Furthermore, by allowing evolution of candidate sequences in the pool a higher chance of success in obtaining the best solution (aptamer) is more likely compared to SELEX because SELEX interrogates a fixed population of possible solutions.

The term evolution encompasses reproduction, recombination, cross-over and mutation of sequences between iterations of the selection process. Evolution may be random, designed or a combination thereof.

It should be noted that because the only thing that differentiates one polynucleotide aptamer from another is its sequence, the properties of that aptamer must therefore be encoded in its sequence.

Assignment of aptameric potential is by means of one or more measured or calculated properties specific to each sequence. For example, aptameric potential may be based on the abundance of the sequence in the ligand-enriched mixture, the relative abundance being compared to previous iterations or a control. Quantification may be combined with other measures of aptameric potential. Such measures are typically derived from the sequence itself and properties imparted by the sequence, such as secondary or tertiary structure predictions, hydrophobicity, similarity to known aptamers etc. Compounded measures that mathematically combine or aggregate these measures may also be appropriate. The potential of certain general sequence motifs, may also be used to estimate the aptameric potential of sequences. The method of determining the relative or absolute aptameric potential of a candidate sequence from its measured statistical or sequence characteristics (or others) is termed as a 'fitness function'. This is in line with standard terminology for those skilled-in-the-art of evolutionary search heuristics (14). Other terms also exist for the same concept, such as 'objective function'. Expressed non-technically, this is an objective measure, usually a numerical score, of a candidate aptamer's potential.

A feature of the present invention is allowing the highly aptameric individuals to undergo small, random compositional changes, such as a single alteration of sequence, and crossover recombination of the sequences, thereby creating a new pool of stronger candidate aptamer sequences. A significant advantage of allowing evolution of the sequences is that it allows the generation of sequences and motifs that may not have been present in the initial candidate pool, thus enhancing the likelihood of identifying optimum aptamers for a target protein. Another significant advantage of the method is that it is only the 'fittest' candidate sequences that are allowed to recombine with each other and undergo mutation, thus generating a child population of putatively fitter and novel aptamer sequences.

A fundamental difference between the scheme of the present invention and SELEX is that SELEX does not easily allow the introduction of mutations or changes in the sequences under study. Indeed, the only way mutations could occur is by accident during the amplification step when bound sequences are amplified by PCR. However, such mutations are likely to be too rare to affect the process i.e. the overall composition of the population of sequences under study. Also, SELEX does not enable or allow recombination or crossing-over, otherwise termed "recombination or reproduction", of sequences between aptamer species, nor rational intervention to change the aptamer sequences. Furthermore, SELEX schemes do not allow sequences to be assessed, for example for their 'fitness' as aptamers, and rationally manipulated between rounds of selection.

An example of rational intervention may be to ensure that all aptamer sequences at any iteration contain a particular sequence motif. This may not be the case after mutation and recombination. Hence the rational intervention acts as a filter or constraint on randomness. Importantly, this can improve the efficiency of the selection process as it enables prior knowledge, for example of known protein binding motifs, to be built into the population of sequences under study and maintained. This allows a human being to direct and constrain the evolution whilst not fully determining its outcome.

In a further example, by monitoring the diversity of the sequence pool at each iteration, the population can be encouraged to find several solutions (aptamers) to several proteins in parallel. This can be accomplished by identifying, monitoring and directing the evolution of several sub-populations of distinct sequences within the whole population. This would not be possible with SELEX because, unlike the proposed invention, SELEX does not allow quantification of the bound aptamers at each iteration of the process nor uses this information to make inferences and decisions about each sequence between each iteration of the aptamer pool in a manner that positively influences the overall outcome.

So-called 'Next generation' polynucleotide sequencing techniques require the separation of individual molecules of DNA or RNA or other polynucleotide sequences onto a surface, such as a bead or chip, thereby creating a single molecule array of sequences. The array has a surface density that allows each molecule to be individually resolved, for example by optical microscopy. Sequencing of the polynucleotide molecules on the array allows 'digital', i.e. absolute, counting of the sequences and, thus, direct quantification of the sequences present on the array. In some technologies, sequences may be clonally amplified once arrayed to strengthen and/or clarify the signal from each sequence. Nonetheless, quantification is obtained by counting the occurrence of sequences on the array and not the signal produced from each amplicon. Examples of suitable sequencing and quantification techniques may be found in publications such as WO 00/006770 and Branton et al (21).

In the proposed invention, manipulation of the candidate aptamer sequences is achieved by using massively parallel DNA sequencing such as those techniques embodied in 'second generation', 'next generation' or 'third generation' DNA sequencers. Use of massively parallel sequencing allows the ligand-enriched candidate aptamers to be quantified and sequenced in parallel, thereby providing information on fitness measures derived from their abundance and other fitness measures, derived from their sequences, at the same time. It will be appreciated, given the performance of massively parallel sequencers, that such a scheme will significantly reduce experimental time and costs of discovering aptamers under the proposed scheme.

Thus, another example of rational intervention (or human direction) would be, having examined and counted the aptamer sequences under study, a flaw is noticed in the efficiency of the sequencer itself that is compromising the representation of certain sequences. This can be compensated for by biasing the composition of subsequent populations.

Accordingly, in a preferred embodiment, aptameric potential is measured by quantifying each sequence obtained in step c). Ideally, quantification is carried out using a single molecule array of the sequences or similar device that can sequence and count individual molecules in a massively parallel fashion. In particular, sequencing or partially sequencing sufficient to identify each sequence on the array, in combination with counting of each sequence, is carried out to achieve quantification. Alternatively, the sequences may be quantified on a clonal array, in which each sequence is amplified after being arrayed on a surface. In this way, the primary fitness measure may be counts on an array representing the frequency of a given candidate aptamer sequence in the population under study. Once a primary fitness has been obtained, bioinformatic data, such as similar motifs or secondary structures, derived from the nucleotide sequence or molecular composition of each candidate aptamer and obtained during quantification, may be used in addition to drill down into the ligand-enriched sequences and obtain further fitness criteria. These calculated but composition-dependant properties can be subsequently exploited in the evolutionary generation of the candidate aptamer library for the next round by either building them in, biasing or eliminating them.

The present invention harnesses the ability of currently available technology to separate and quantify individual sequences in a massively parallel fashion and down to single molecule sensitivity. It also allows the study of a complex and diverse population of sequences. When screened against a single protein, a candidate aptamer sequence that is found to be more abundant in the bound fraction will have a higher fitness than a sequence of which only one copy is bound by virtue of the fact that the method searches for candidate aptamer sequences that stick (bind) to the protein under study. This is a primary property that defines an aptamer. When screened against a complex mixture of proteins, other statistical properties derived from the quantifying procedure will be required to identify the aptamer(s). The advantage of massively parallel sequencing is that it allows each and every sequence to be counted and hence quantified. This is in contrast to, say, an antibody assay in which the resolution cannot be as high.

Accordingly, the counting of the aptamers and other measured, calculated or historical statistics generated from their sequences, can be used and combined into a 'fitness function'. This enables the physical execution of more sophisticated and more successful evolutionary search heuristics at the molecular level than that embodied in SELEX. As with such sophisticated heuristics in the computational domain, it is the ability to derive such a 'fitness function' itself and to apply it to refine subsequent iterations of the population of molecules under study that is important, rather than the specifics of the given 'fitness' measure itself. It will be appreciated that the invention will allow many such explorations, thereby allowing learning of the optimal general 'fitness' properties of aptamers or to derive context specific 'fitness' measures, for example to certain classes of proteins.

As information about candidate sequences and motifs is built up, knowledge of particular features can be built in to later candidate pools or new pools for identifying aptamers to related or similar proteins. Equally, sequences and motifs that are found not to be effective can be positively excluded from a candidate pool.

Also, sequences of known aptamers to known proteins can be positively excluded from a candidate pool if an aptamer with selectivity for a different protein is required. This assists in ensuring that discovered aptamers are more likely to be specific to this protein, a major requirement for useful aptamers. Alternatively, if sequences and/or motifs are chosen that provide selectivity and specificity to a particular family of proteins, these sequences and/or motifs may be built into a candidate aptamer pool that is then used to identify aptamers selective for these protein subtypes.

All of these advantages are driven by having knowledge of the aptamer sequences, their relative 'fitness', as well as other calculable characteristics derived from their sequences or from their quantitative behaviour under the selective scheme.

The algorithmic encoding scheme used by Genetic Algorithms mirrors the actual compositional nature of the invention. These algorithms encode search problems into 'genomes' by analogy of characters or numbers (or bits) that are subjected to iterative changes, such as cross-over recombination and selection/amplification, albeit within a computer's memory. In accordance with the present invention, these processes are executed using the actual molecules under study. The molecules, in this case polynucleotide sequences, themselves encode the possible solutions to the search and it is the assessment of their properties, such as their stickiness to proteins (as manifest by quantification), which are also encoded in their sequences, that drives the method (15). Thus, the invention is the physical embodiment of a genetic algorithm. This is enabled by the use of massively parallel DNA/RNA sequencing and also the fact that aptamers can be discrete polymeric molecules whose aptameric properties are encoded in their sequence.

To be more explicit, the use of massively parallel sequencing enables the implementation of optimised semi-rational/semi-random evolutionary search strategies for identifying aptamers specific to a protein target or multiple protein targets. For example, known sequence motifs that have previously been shown to be effective against proteins which are similar to the one under study can be preferentially selected as part of both the initial library generation and as part of the fitness selection. In this way, the process is intrinsically and favourably biased towards a high quality or 'fit' solution that contains these motifs where these motifs may also be a prerequisite for any solution. However, sufficient randomness in the library generation and subsequent mutational alteration of the motifs can be used to ensure that new, but similar, sequences are found to bind the protein under study. The fitness function can be designed such that similar, but sufficiently different, sequences to those already found to a previous protein are selected, ensuring both success and specificity in selection of suitable aptamers. This also facilitates the accumulation over time of a catalogue of sensitive and specific aptamers to many proteins. Such 'non-overlapping' sub-populations of distinct aptamers that are operating against one protein and not another can be used subsequently simultaneously to probe and measure several proteins in parallel.

Because massively parallel sequencing allows multiplexing, aptamer libraries to more than one protein may be generated and screened at the same time. Similarly, the invention allows for many high quality but different aptamers (at the sequence level) to be selected against single or multiple protein targets in parallel.

In addition, because massively parallel sequencing allows the quantification of each sequence species, and each species can represent a single protein, the proposed method uses genomics to extend the power and dynamic range of proteomics.

In a specific embodiment of the invention, a diverse library of designed, random, or semi-designed sequences is screened and selected against in vitro sets of folded proteins derived from biological material e.g. serum or plasma. It will be appreciated that the library of sequences may be generated by any method.

Sequences that do not bind proteins are removed or eluted. To achieve this, various known options are available. For example, a single protein or a complex protein sample may be immobilised on a solid support. Stringent washing may be performed to remove unbound and weak binding sequences. Another option is the use of reversible cross-linking of the sequence on the protein targets (photoaptamers).

The remaining bound sequences are removed from their protein hosts and run through a massively parallel sequencer where they are sequenced and counted.

As a specific example of massively parallel sequencing, the bound sequences are randomly arrayed on a surface, such as a bead or a chip. The sequences are optionally amplified cyclically yielding groups of clonal single stranded molecules at discrete x and y coordinates on the surface or on an individual bead. A suitable DNA sequencer then executes a stepwise chemistry consisting of reagents that allow the determination of one base on each complementary sequence per cycle or to monitor the incorporation of bases in real time. An illumination and imaging system allows this process to be photographed such that the sequences of the original candidates can be obtained. Regardless of the specifics of the sequencing technology, a complementary sequence mirroring each bound candidate sequence is built up. Typically such technologies are able to sequence in excess of 40-300 million fragments of DNA at up to 75 base pairs in length and these numbers are increasing rapidly as the technologies improve. This process currently takes less than 1 to 3 days from sample preparation to sequencing output and these timescales are shortening.

It will be appreciated that other massively parallel methods that fall into the category of "next generation polynucleotide sequencing" may be used and the present invention is not limited to the specific example provided. "Next generation polynucleotide sequencing" is a term generally coined to described DNA/RNA sequencing platforms that have appeared since 2004. Since 2008, another generation of sequencing platform with improved characteristics is now being coined as "third-generation". Their common characteristic is that they use a different sequencing chemistry from the old technology that was based on "Sanger" sequencing. The new platforms use new chemistries and generally have very high throughput and much lower costs. This has been achieved through the ability to parallelise the sequencing reactions to a very high degree. The new platforms typically, but not exclusively, proceed by synthesis or strand extension (building), unlike the Sanger method which works by snipping off bases (degrades). In addition, the new platforms operate on tiny numbers of single or of clonal molecules, unlike the Sanger method which has a very large DNA sequencer molecule to base measurement ratio.

It will also be appreciated that while reference is made to DNA sequencing, the DNA sequencing technology may also be used with RNA or PNA (peptide nucleic acid) sequences. Thus, reference to next generation sequencers or sequencing encompasses DNA, RNA and PNA, as well as all other chemical variants of nucleic acid based polymers and their analogues that are suitable for use in the method of the present invention. All of the new sequencing technologies, whether "next-generation" or "third-generation" are able to sequence individual molecules or their clonal copies in a massively parallel and highly efficient manner.

The use of 'sequence counting' i.e. to quantify the absolute or relative abundance of sequences in complex biological samples (such as miRNA) has already been well established and described for such next-generation or massively parallel platforms (18). On an effective massively parallel sequencing platform, the derived sequences complementary to the original candidate sequences should be highly accurate and have few, if any, significant systematic sequence context biases, such as the inability to resolve homopolymers and palindromic sequences or other motifs which a strong structural element. On some platforms, this has already been established by the re-sequencing of large complex genomes (which contain such motifs).

The method of the present invention may be carried out on a single, isolated protein. Alternatively, the method may be carried out on a single protein known to be present within a mixture of proteins.

However, one of the strengths of Genetic Algorithms is that sub-populations may be evolved from a broader population. This is achieved by sub-selecting against different criteria. Thus, in a further alternative, the method also allows the interrogation of many proteins within a mixture, at the same time. This is enabled by the use of next generation DNA sequencing techniques because the techniques allow multiplexing.

When searching for candidate aptamers against multiple proteins, the emergence of distinct populations of candidate sequences can be monitored. The sequence populations may then be grouped and developed in parallel under the general scheme in the invention. For example, distinct aptamers could be identified for different regions of a single protein. It will be appreciated that the number of populations interrogated at any one time will be limited by the dynamic range of the target molecule as well as the sequencing array.

The method of the invention may be used to interrogate a single target or protein (e.g., gel-excised protein) but is particularly suitable for analysing mixtures of targets, including complex protein mixtures. The terms "mixture of proteins" or "protein mixture" generally refer to a mixture of two or more different proteins, e.g., a composition comprising said two or more different proteins or their isoforms.

In preferred embodiments, a mixture of proteins to be analysed herein may include more than about 10, preferably more than about 50, even more preferably more than about 100, yet more preferably more than about 500 different proteins, such as, e.g., more than about 1000 or more than about 5000 different proteins. An exemplary complex protein mixture may involve, without limitation, all or a fraction of proteins present in a biological sample or part thereof.

The terms "biological sample" or "sample" as used herein generally refer to material, in a non-purified or purified form, obtained from a biological source. By means of example and not limitation, samples may be obtained from: viruses, e.g., viruses of prokaryotic or eukaryotic hosts; prokaryotic cells, e.g., bacteria or archeae, e.g., free-living or planktonic prokaryotes or colonies or bio-films comprising prokaryotes; eukaryotic cells or organelles thereof, including eukaryotic cells obtained from in vivo or in situ or cultured in vitro; eukaryotic tissues or organisms, e.g., cell-containing or cell-free samples from eukaryotic tissues or organisms; eukaryotes may comprise protists, e.g., protozoa or algae, fungi, e.g., yeasts or molds, plants and animals, e.g., mammals, humans or non-human mammals. Biological sample may thus encompass, for instance, a cell, tissue, organism, or extracts thereof. A biological sample may be preferably removed from its biological source, e.g., from an animal such as mammal, human or non-human mammal, by suitable methods, such as, without limitation, collection or drawing of urine, saliva, sputum, semen, milk, mucus, sweat, faeces, etc., drawing of blood, cerebrospinal fluid, interstitial fluid, optic fluid (vitreous) or synovial fluid, or by tissue biopsy, resection, etc. A biological sample may be further subdivided to isolate or enrich for parts thereof to be used for obtaining proteins for analysing in the invention. By means of example and not limitation, diverse tissue types may be separated from each other; specific cell types or cell phenotypes may be isolated from a sample, e.g., using FACS sorting, antibody panning, laser-capture dissection, etc.; cells may be separated from interstitial fluid, e.g., blood cells may be separated from blood plasma or serum; or the like. The sample can be applied to the method of the invention directly or can be processed, extracted or purified to varying degrees before being used.

The sample can be derived from a healthy subject or a subject suffering from a condition, disorder, disease or infection. For example, without limitation, the subject may be a healthy animal, e.g., human or non-human mammal, or an animal, e.g., human or non-human mammal, that has cancer, an inflammatory disease, autoimmune disease, metabolic disease, CNS disease, ocular disease, cardiac disease, pulmonary disease, hepatic disease, gastrointestinal disease, neurodegenerative disease, genetic disease, infectious disease or viral infection, or other ailment(s).

Preferably, protein mixtures derived from biological samples may be treated to deplete highly abundant proteins there from, in order to increase the sensitivity and performance of proteome analyses. By means of example, mammalian samples such as human serum or plasma samples may include abundant proteins, inter alia albumin, IgG, antitrypsin, IgA, transferrin, haptoglobin and fibrinogen, which may preferably be so-depleted from the samples. Methods and systems for removal of abundant proteins are known, such as, e.g., immuno-affinity depletion, and frequently commercially available, e.g., Multiple Affinity Removal System (MARS-7, MARS-14) from Agilent Technologies (Santa Clara, Calif.).

While the present invention has particular application to the identification of aptamers specific for proteins, it is to be appreciated that the invention also has an application for the interrogation of other molecules, such as metabolites and potential small molecule and biological therapeutics.

The method described above focuses on quantifying aptamer sequences through sequencing. For the purpose of generating a library of aptamers specific for a single protein, the sequences of the aptamers may not need to be specifically investigated until the library has been finalised. Thus, the method may further include obtaining the sequences of only the final pool of aptamer sequences.

A significant advantage of the method is that small—picomolar or even femtomolar—quantities of material are required. If a 40mer DNA aptamer sequence is prepared using the four bases, A, C, G and T, there are potentially $1.2 \times 10^{24}$ combinations available. Thus, 1 mole ($6.2 \times 10^{23}$) could only, at best, contain 5% of all the possible sequences and such a preparation would weigh over 1 kg. 1 picomole will contain approximately $1 \times 10^{11}$ molecules, so 1 ml of picomolar unique aptamers will contain $1 \times 10^8$ molecules. If 17 base pairs in the 40mer are fixed i.e. as a 'motif', leaving 23 variable and/or random base pairs, since 1 picomole will contain up to about 70 copies of each possible sequence, 1-10 ml of picomolar solution should contain between 1 and approximately 10 copies of each sequence. Thus, the quantification apparatus (i.e. massively parallel sequencer) can and should exceed, in sensitivity, both the affinity of aptamers for proteins and the native concentration of most proteins in unmodified biological samples.

A next generation sequencing device, such as that sold by Illumina®, typically has 330×8 imaging areas on its surface, on which it should be possible to extract cleanly 25000 sequences or so per imaging area. Therefore, currently, it should be possible to interrogate about $1 \times 10^8$ 40mer sequences per chip per run. Accordingly, the technology should allow 1:1 observation of picomolar aptamers in solution. Thus the technology has a dynamic range that spans the dynamic range of proteins in native samples. The performance of such sequencing technologies is improving over time.

Once a library or population of aptamers specific for a particular protein has been devised, the sequences of the aptamers may be used to build rational knowledge of the structure, function and binding characteristics of the aptamer population for the specific protein, or vice versa. This, in turn, may be used to investigate the protein further and to refine other parameters and/or features of an aptamer library. These refinements can be applied either during the initial library generation and/or during rounds of iterative selection under the scheme proposed. Indeed, over time, the sequence/structural relationships between identified aptamers and proteins will be built up and can be used as input into the design of initial aptamer libraries to explore different and other parts of the aptamer space with differing motifs.

Such information may also be used to evaluate proteins having similar structures to the initial protein of interest. In this way, having found aptamers to certain classes of proteins, similar proteins may be investigated and interrogated by utilising rationally chosen starting aptamer libraries based on prior knowledge of proteins in the same class. Knowledge of the library sequences for one protein, or a particular domain, may also be used to assist in the design of an aptamer pool for related proteins and other members of protein families on the assumption, or demonstrated and measured characteristic, that similar aptamer sequences bind to the surfaces of similar proteins.

Discarded aptamer sequences may also be mined for information. For example, the statistical and calculated properties (e.g. structure) of these sequences may be used to characterise the general properties of weak aptamers. Such information provides useful knowledge when designing initial aptamer libraries, enabling a shortcut to limiting the randomness of an initial library as the sequence level.

In an alternative embodiment, an intermediate step may be to examine the aptamer tags (sequences) bioinformatically and to refine them rationally, thus ensuring an evolutionary progression of the population towards diverse yet highly specific tags. Bioinformatic data includes sequences that result in particular secondary and tertiary structures, and sequence complementarity between candidate sequence and protein.

As outlined previously, characteristics can be calculated, tabulated, correlated and stored for given aptamer sequences and other biological data such as protein families, fold domains etc. These bioinformatic characteristics can be used to refine initial library generation. They can also be used as part of the 'fitness function' between rounds of selection of the candidate aptamer sequences in order to shape and improve the characteristics of the population at each stage.

Proteins in blood are a particular target for the identification of markers of disease states and drug treatments. It is widely assumed that the amounts and/or conformation of proteins in the blood should be statistically related to such states in a manner that outweighs intrinsic natural variability. Blood and other body fluids are a particular target because they bathe affected tissues, transport vital proteins and can be obtained for testing using relatively cheap and straightforward procedures during a medical consultation.

However, proteins in blood have a very large range of concentrations, with a small number of proteins accounting for over 99.9% of all proteins and the rest occupying a distribution from picogram to milligram per milliliter (19). Thus, a high abundance of a small population of proteins masks vital yet rare proteins also present in the protein mixture.

The method of the present invention allows the identification of aptamer to proteins present in a biological sample in low or extremely low abundances. Thus, in a further embodiment, the method further comprises removing the very highly abundant candidate sequences that are found in early (first and/or second) and/or other rounds of iteration. Given that a sequencing array has a finite number of "slots", highly abundant candidate sequences will occupy most if not all the slots, thereby masking any less abundant candidate sequences and providing a skewed view of the dynamic range of underlying proteins. By removing the very highly abundant candidate sequences, in either absolute or relative terms, from the sequence pool, candidate sequences specific for the highly abundant proteins can then no longer be interrogated and this particular population of proteins within a complex mixture is effectively ignored, even though the proteins are still present in the mixture.

Removal of fit sequences to one highly abundant protein will either reveal another highly abundant candidate sequence, or will reveal candidate sequences to lower abundant targets.

This is another example of rational intervention to bias the discovery of aptamer sequences towards lower abundant proteins. Other balancing selections will also be required in the fitness function, such as low variance on the putative low abundance aptamers between replicates of the same iteration, and/or the preference of certain known sequence motifs. This would help to ensure that low abundance but 'fit' sequences are selected from the background noise of non-specific or random sequences.

An advantage of this additional step is that manipulation of the protein mixture to remove the very highly abundant and common proteins is avoided. In this way, the protein mixture is more truly based on the natural sample and, by inference, any information about the proteins derived from the mixture is more likely to reflect more accurately the natural situation for each protein. This use of the natural state of proteins has the added advantage that it also allows the selection of aptamers that are specific towards proteins having chemical modifications or other post-translational modifications which are common in nature.

The highly abundant candidate aptamers may either be simply ignored or the population may be subtracted or removed from the pool. Removal may be achieved, for example, by hybridisation on a solid support containing complementary probes to the abundant sequences. Removal may also be an example of rational intervention, in that particular candidate sequences are excluded from subsequent iterations by programming a DNA synthesiser appropriately to generate a new sequence pool with all of the desirable characteristics that infer 'fitness' with the exception of the sequences that bind highly abundant proteins. This new pool is then carried forward in subsequent rounds of selection under the general the scheme that comprises the invention.

A panel of only the least abundant candidate sequences from the first step may then be focused upon and subsequently used. Thus, the quantitative power of the sequencer may be focussed on only very low abundant candidate sequences and, by proxy, proteins present in a protein mixture in low abundance. This is currently not possible with either conventional MS (Mass Spectrometry) based technology or SELEX.

Iterative subtraction of highly abundant candidate sequences should allow interrogation of the lower abundance candidate sequences. To ensure that any binding is selective and not purely chance, the candidate sequences may be spiked with a known aptamer sequence in a known quantity and the sequences run against a mixture of proteins, including the protein to which the known aptamer binds being present in a known quantity. Alternatively or in addition, low variance across a number of replicates should mean that the candidate sequences under interrogation are highly likely to be binding (sticking) to a protein.

Accordingly, the method of the present invention addresses one of the main problems of proteomics, namely how to cope and deal with highly abundant proteins. This is achieved by rationally excluding candidate sequences that bind to these proteins. These proteins are ignored in subsequent rounds of measurement and selection. The mutation/cross-over process may cause the re-appearance of some candidate sequences that bind to high-abundance proteins but these sequences can also be rationally eliminated at each iteration of the process as described previously. Careful selection of low abundant candidate sequences, with strong sequence properties and low variance on their quantitative measurements between iterations, should allow convergence onto a population of potential aptamers (or subset) that binds specifically and sensitively to low abundant proteins.

In a further embodiment, by counting the candidate sequences and comparing them to a control population, the abundance range of candidate sequences in each iteration may be also monitored. This may be further used to refine the fitness-based selections. An example would be, during the first round of selection, the population of selected sequences is compared to those present in the initial unscreened library. A significant change in sequence composition and statistical prevalence of certain sequences (perhaps conforming to some model) may indicate relative success. If the first few rounds of selection do not produce a candidate sequence pool that is significantly different in composition from the initial population, the pool and experiment may be judged failures.

It will be appreciated that once one or a library of candidate aptamer sequences has been identified by the method of the present invention, the sequence(s) must be validated as an aptamer. This may be achieved by replicating binding and quantification of the candidate sequence against multiple copies of the same original sample or across multiple different samples. If there is poor replication or high variability between samples then the candidate sequence is unlikely to be specific for a one target. A suitable method for such validation is described in co-pending European Application No. 07020049.8.

The invention will now be further described by way of a non-limiting examples.

EXAMPLE 1

In this example, for comparison with SELEX, a set of aptamers is sought against a single protein that may be present in solution or immobilised.

A population of polynucleotide sequences, such as DNA or RNA, is represented as a motif or pattern. For example, the sequences GGCT and CCGA can be represented by one pattern GGC(A/T) where '/' means 'or'. A sophisticated set of IUPAC single letter codes exists to represent sequence patterns enabling representation of a multiplicity of sequences with their commonalities highlighted (20).

In this example, DNA aptamer motifs are selected and semi-random libraries synthesised using known techniques (11). This is referred to as the 'candidate library'. The diversity of the libraries may be in any range capable of synthesis. In this example rational prior knowledge is used to favour DNA sequences that have certain secondary structures by virtue of self-similarity and annealing. A control library is also constructed of purely random sequences of the same length. This is called the 'random library'.

Both libraries are then screened against a single protein under conditions selected so that non-binding aptamer sequences may be discarded as embodied in conventional SELEX schemes.

The surviving aptamer DNA sequences, i.e. those sequences bound to the protein, are arrayed on a next generation DNA sequencer of suitable resolution and dynamic range, following unbinding of the aptamers from the protein. This procedure is replicated for refinement of the statistical significance of resulting measurements.

Every molecule on the array is sequenced and counted such that aptamers present in the surviving libraries are identified and counted. The numbers of sequences present on the array should represent the proportion of the molecules in the originating populations, in line with normal statistical sampling procedures. The accuracy of the measurements and any statistical sampling problems, especially with rarer aptamers, can be ascertained via the measurement of variance from the replicates of each library.

A differential comparison of the first iteration(s) of selected aptamers to the initial unselected library is made. This also enables an assessment of the success and efficiency/diversity of the library synthesis. Similarly a differential analysis is performed of the purely random library of aptamers versus its unselected counterpart. If the selected/exposed semi-random library does not differ significantly from the unexposed/random library it can conclude that the aptamer selection is not suitable and that the library is unpromising. At this point trial of this library may be halted and another library synthesised with differing characteristics at the sequence level.

If the candidate library is sufficiently divergent after the first iterations(s) from the non-exposed candidate library and/or from the random library, the library will be used and developed further.

From an initial aptamer pool of any size, a sample in the range of $10^7$ to $10^9$ aptamers will be sequenced on the array. Future generations of sequencers will allow a higher dynamic range. Given the initial candidate library diversity and the results of the sequencing and counting (and controls) in the previous step, the quality of the aptamer motifs may be assessed after the first iteration. As described, either the aptamer population may be progressed if considered promising or, alternatively, a new initial candidate motif library may be generated. For example, if the distribution and variance of surviving aptamers is very different to the initial library as measured from the controls, such a library would be favoured for progression.

The first iteration provides data from the experimental condition and control:

TABLE 1

| Sequence | Abundance | Sequence property A* | Over control** | Fitness |
| --- | --- | --- | --- | --- |
| GCTG | 30000 (+/−30) | 23.7 | 4000 | 0.76 |
| GCTT | 1000 (+/−100) | 21.5 | 2000 | 0.68 |
| AAAT | 23 (+/−50) | 2.3 | 300 | 0.3 |

*any arbitrary property derivable from the DNA sequence itself
**any significant quantitative measure relative to a control In Table 1, each aptamer sequence, its quantity and variance, bioinformatic properties derived from the sequence, such as secondary structure, and an overall measure of sequence fitness via the aforementioned 'fitness function', can be calculated. In use, the table will have thousands or tens of thousands of entries with one row for each unique aptamer sequence. Columns contain aggregated measures for that aptamer sequence. The table shown is for illustrative purposes only.

Fitness calculations from multiple scores have been well described in the literature for genetic algorithms (14, 15) and may, purely for example, involve the Bayesian combination of multiple probabilities. Any suitably calculable measures of fitness may be used based on either the measured abundance of the sequence or the sequence itself (and any derivable properties). In the simplified example provided in Table 1, the motif GCT is clearly favoured and GCTG especially shows as being heavily weighted by its quantity relative to the control. In this way, by application of a fitness measure, each candidate aptamer sequence can be tabulated and assessed for its potential as an aptamer. The score that is obtained as a measure of fitness is used to assess whether the given candidate sequence survives to the next iteration and may also be used to determine whether the sequence is allowed to reproduce (cross over) or be subject to a mutational process that changes its sequence composition. After applying these processes other new aptamer sequences may be derived in addition to the original.

Low variance between replicates may also be an example of a statistic that demonstrates specificity for a given motif or sequence to a protein. Replicates of the experimental measurement may thus be used to refine the derived statistical measures exemplified in Table 1. A key aspect of the invention is that suitable statistics can be derived by experimentation and learning.

On the basis of the information gathered at this stage, a new synthetic aptamer population, based on measured statistics, bioinformatics and rational analysis from the results of the first generation, may be generated. In this example, and purely for illustration, rather than conventional amplification as used in SELEX, the library is re-synthesised on the DNA synthesiser. This re-synthesis may include the programming of the crossover combinations of motifs derived from the tabulation of fit sequences, as shown in Table 1, and some degree of random mutation in the new sequences at certain positions and not others. In this way, sequence diversity in the aptamer population is maintained at a suitably diverse level in early iterations. In accordance with conventional genetic processes the subsequent new population, derived from the fittest individuals of the previous population (Table 1), should also be as 'fit' or 'fitter'. As the fitness of the generations of populations converges, intervention in the population diversity will decrease. By using rational design, mutational and crossover procedures, the diversity of candidate aptamers can also be maintained in early populations. This will ensure that the final solution does not encounter a premature "local minimum" or other search-stopping conditions as described in other documented embodiments of such algorithms (15).

The new candidate library ($n^{th}$) is now exposed to the protein under study. The surviving and bound aptamers are eluted and re-arrayed on the sequencer and the general assessment procedure above is repeated.

The previous sequencing iteration (n−1) of the candidate library may become the control going forwards as the new population is sequenced and counted and results tables generated for the current iteration (n) replacing the values in Table 1. Rapid dominance of certain sequences may be seen, reflected in their abundances and variance relative to the last iteration (n−1), as well as between replicates of the current iteration. Equally, this trend may not be seen. In the latter scenario, the number of 'mutations' (random changes to the aptamers during synthesis) may be increased to accelerate the evolution and diversity of the population of sequences under study. Either way, asymptotic convergence of the population towards a stable set of solutions, i.e. aptamers, can be tracked and optimised if necessary and as required. Such a rationale also ensures that the rate of ascent of the population, towards a stable plateau of fitness and composition, can be maximised.

Iteration of the population of candidate aptamers is carried out until a stable population of candidate solutions (aptamers) is achieved. In later iterations, once the dominance of certain sequence motifs becomes apparent, it may be necessary or desirable to amplify the sequences between iteration, rather than re-synthesise the sequences. Alternatively, alternate rounds of synthesis and amplification may be used.

The resulting sequences are likely to be strong aptamers for the protein under study and it is expected that several equally viable aptamers may be found. Each viable aptamer may or may not be structurally different at the sequence level.

Once one or more suitable aptamers have been identified, the aptamers may then be modified chemically, for example using nucleotide analogues, to increase stability and other desirable properties. The population may then be re-screened using the same or other procedures to confirm specificity and other properties of each aptamer.

Thus, for a given protein, a library of sequences shown to behave as aptamers for that protein can be built up. Most importantly because changes to the composition of the sequences have been allowed during iterations, both randomly and rationally guided, a population of strong solutions may be found that were not necessarily present in the initial candidate aptamer library.

EXAMPLE 2

While the above example is directed to the generation of an aptamer library to a single known protein, the process may also be used against mixtures of known proteins in vitro. This is because the ratio of possible aptamers to proteins is so high. In this case, diversity of motifs at the sequence (and implicitly the structure) level is important. An early population of diverse but functional sequences is thus an important characteristic of the present invention.

In this example several known proteins are isolated for aptamer selection. The method proceeds as in Example 1 except with the aim of selecting and managing several candidate aptamer libraries in parallel. This is accomplished by grouping the aptamer libraries together in one candidate library, or starting with one sufficiently diverse candidate library to encompass aptamers to all proteins under study. The method described in Example 1 is followed, with the addition that, after early iterations, the aptamers are grouped or clustered together in a manner already described in Genetic Algorithms (16), to generate several conceptual tables as shown in Table 1. In Example 1, the grouping can be based on 'clustering' or other methods using the measured characteristics embodied in the Table 1. In this case the intervention between selections operates to maintain conceptually distinct tables—representing sub-populations of aptamers—that are notionally representative of the mixture of proteins under study. In its simplest embodiment this is a form of multiplexing.

At the end of the selection process, aptamers specific to proteins in the mixture under study will be obtained. In this case it may not be known which aptamer subsets bind which proteins. This can either be resolved later using other experimental techniques, or may not be necessary. In the latter case, it is possible to generate and use 'anonymous' aptamers to known proteins, provided the aptamers and proteins are to be deployed and used together.

Alternatively, prior knowledge of the specificity of certain aptamer sequence motifs to certain protein structure may be used to imply which aptamers are matching which proteins.

In both Example 1 and 2, the specificity of the identified aptamers to the given proteins they have been selected against should be demonstrated as an additional step.

This additional step may also accomplished using next generation sequencing by exposing the aptamers to a complex biological sample that contains a known amount of the protein against which it was selected. The measurement(s) of the aptamer(s) should not be confused by non-specific binding to proteins present in the sample other than the one they were selected against. This can be tested using counting statistics generated by the act of arraying and sequencing exposed aptamers.

EXAMPLE 3

Ideally, the specificity of aptamers to their respective proteins is built into the selection/generation process. This is not possible with SELEX schemes and schemes against single proteins or small subsets.

In this example, the method proceeds as described in Example 1. However, in this example, the aptamer library is exposed to a native complex biological sample. This experiment is highly replicated.

Firstly, aptamers that are very highly represented on the array will be seen. Some or all of these highly represented aptamers may also have a high degree of variance between replicates. In the former case, it may be reasonably concluded that the aptamers are binding highly abundant proteins. If their variance is high it is reasonable to conclude that the aptamers lack specificity.

In the next round of synthesis, these abundant or variance ridden aptamers are excluded. The method of the invention is then carried out as outlined in Example 1 until the sequencing array contains a diverse set of sequences of low relative representation (perhaps to some control) and very low variance between replicates. In this case, aptamers that bind the highly abundant proteins in the sample and/or those with low specificity have been effectively excluded.

The subsequent aptamers can be used individually or in groups to repeat the method as set out in Example 2 using a mixture of known proteins. The identified aptamer sequences may provide the 'motifs' used to generate the semi-random libraries required in the simpler examples. In this way, the library will be pre filtered for sensitivity and specificity—a common cause of failure of antibody based methods.

In a further step, the population may be proceeded with en masse to identify a large number of aptamers against unknown low abundance proteins using the general scheme in Example 2. In this case the proteins to which the aptamers are binding are unknown. Identification of the proteins will be elucidated in a further step using other technologies. However it is conceptually possible to develop a set of 'anonymous' aptamer probes to unknown low abundance proteins.

This does not limit their utility as they can then be deployed to measure these proteins in many samples. The aptamers are now proxies for these proteins and statistically significantly varying aptamers (viz proteins) can thus be measured between samples i.e. discover biomarkers. Having accomplished this, and having a suitable aptamer in hand, the aptamer can be subsequently extracted and used to identify the protein for which it is a proxy. In this way it is possible to discover aptamers to complex mixtures of anonymous low-abundance proteins, deploy them in biomarker discovery, find the significant aptamer(s) and thence identify the proteins as a final step, rather than the first as with the current state-of-the-art.

REFERENCES

1. "A programmable biomolecular computing machine with bacterial phenotype output." Kossoy E, Lavid N, Soreni-Harari M, Shoham Y, Keinan E. Chembiochem. 2007 Jul. 23; 8(11):1255-60.
2. "DNA molecule provides a computing machine with both data and fuel." Benenson Y, Adar R, Paz-Elizur T, Livneh Z, Shapiro E. Proc Natl Acad Sci USA. 2003 Mar. 4; 100(5): 2191-6

3. "Solving satisfiability problems using a novel microarray-based DNA computer." Lin C H, Cheng H P, Yang C B, Yang C N. Biosystems. 2007 July-August; 90(1):242-52
4. "DNA computing using single-molecule hybridization detection." Schmidt K A, Henkel C V, Rozenberg G, Spaink H P. Nucleic Acids Res. 2004 Sep. 23; 32(17): 4962-8
5. "Fast parallel molecular algorithms for DNA-based computation: factoring integers." Chang W L, Guo M, Ho M S. IEEE Trans Nanobioscience. 2005 June; 4(2):149-63
6. "Functional RNA microarrays for high-throughput screening of antiprotein aptamers." Collett J R, Cho E J, Lee J F, Levy M, Hood A J, Wan C, Ellington A D. Anal Biochem. 2005 Mar. 1; 338(1):113-23
7. "Nucleic acid evolution and minimization by nonhomologous random recombination." Bittker J A, Le B V, Liu D R. Nat Biotechnol. 2002 October; 20(10):1024-9
8. "Aptamers come of age—at last". Bunka D H, Stockley P G. Nat Rev Microbiol. 2006 August; 4(8):588-96
9. "Aptamers: molecular tools for analytical applications." Mairal T, Cengiz Özalp V, Lozano Sanchez P, Mir M, Katakis I, O'sullivan C K. Anal Bioanal Chem. 2007 Jun. 21
10. "Aptamers as tools for target validation. Blank M, Blind M. Curr Opin Chem Biol. 2005 August; 9(4):336-42
11. "Methods developed for SELEX. Gopinath S C. Anal Bioanal Chem. 2007 January; 387(1):171-82
12. "Aptamers-based assays for diagnostics, environmental and food analysis." Tombelli S, Minunni M, Mascini M. Biomol Eng. 2007 June; 24(2):191-200
13. "SELEX-A (r)evolutionary method to generate high-affinity nucleic acid ligands." Stoltenburg R, Reinemann C, Strehlitz B. Biomol Eng. 2007 October; 24(4):381-403
14. "Genetic Algorithms in Search, Optimization, and Machine Learning." Goldberg, D. E., Addison-Wesley, USA, 1989.
15. "Genetic Algorithms+Data Structures=Evolution Programs." Michalewicz, Z. 3rd ed., Springer, 1996.
16. "Evolution Algorithms in Combinatorial Optimization," H. M☐uhlenbein, M. Gorges-Schleuter, and O. Kr☐amer, Parallel Computing, 7, (1988), 65-88.
17. "Complex SELEX against target mixture: stochastic computer model, simulation, and analysis". Chen C K. Comput Methods Programs Biomed. 2007 September; 87(3):189-200
18 "Elucidation of the Small RNA Component of the Transcriptome." Lu et al. Science 2 Sep. 2005: 1567-1569.
19 Qian W. J. et al., Mol Cell Prot (2006) 5(10) 1727-1744
20 on the world wide web at chem.qmul.ac.uk/iubmb/miscinaseq
21 "The potential and challenges of nanopore sequencing" Branton et al Nature Biotechnology (2008) 26:1146-1153

The invention claimed is:

1. A method for the identification of at least one aptamer to at least one target molecule, the method comprising:
    a) contacting a pool of candidate aptamer sequences with the at least one target molecule;
    b) partitioning unbound sequences from those sequences that have bound specifically to the at least one target molecule;
    c) dissociating the sequence-target complexes to obtain a ligand-enriched mixture of sequences;
    d) assigning to each sequence obtained in step c) a measure of the sequence's potential as an aptamer, wherein the measure comprises a fitness function;
    e) using the measure of step d) to determine the aptameric potential of the ligand-enriched mixture;
    f) allowing evolution of some or all of the sequences obtained in step c) using information obtained in step e) to create a new candidate aptamer pool; and
    g) repeating the steps a) to f) using the new candidate aptamer pool created in step f) as the input pool of candidate aptamer sequences in the next iteration of step a) until the aggregate aptameric potential of the candidate pool reaches a plateau, wherein sequences present in the final candidate aptamer pool are optimal aptamers to the at least one target molecule, thereby identifying the at least one aptamer.

2. A method according to claim 1, wherein the at least one target molecule is a protein.

3. A method according to claim 1, wherein the at least one target molecule is a single, isolated protein.

4. A method according to claim 1, wherein the identity of one or more of the at least one target molecule is known.

5. A method according to claim 1, wherein the at least one target molecule comprises multiple proteins in a mixture of proteins.

6. A method according to claim 1, wherein the at least one target molecule is a known protein present in a mixture of proteins.

7. A method according to claim 5, wherein the mixture of proteins is derived from a biological sample.

8. A method according to claim 7, wherein the biological sample is a bodily fluid.

9. A method according to claim 8, wherein the bodily fluid is blood or derived from blood.

10. A method according to claim 8, wherein the bodily fluid comprises serum or plasma.

11. A method according to claim 1, wherein the aptamer sequence comprises DNA, RNA, PNA (peptide nucleic acid), or variants or combinations thereof.

12. A method according to claim 1, wherein the aptamer is between a 30mer and a 60mer.

13. A method according to claim 1, wherein the aptamer is a 40mer.

14. A method according to claim 1, wherein the aptameric potential is measured by quantifying the candidate sequences in the ligand-enriched mixture.

15. A method according to claim 14, wherein the quantification step is carried out by sequencing at least part of each candidate sequence.

16. A method according to claim 15, wherein the sequencing step is carried out on a single molecule array or a clonal single molecule array.

17. A method according to claim 1, the method further comprising arraying sequences in the ligand-enriched mixture onto a surface before step d).

18. A method according to claim 17, wherein the method further comprises amplifying the arrayed sequences.

19. A method according to claim 1, wherein the measure of aptameric potential further includes at least one measured, calculated or bioinformatic property.

20. A method according to claim 19, wherein the bioinformatic property comprises secondary structure prediction, tertiary structure prediction, self-similarity, informational complexity, similarity to known aptamer sequences, sequence motifs or combinations thereof.

21. A method according to claim 1, wherein members of the ligand-enriched mixture of sequences having an aptameric potential of greater statistical significance, as compared to the entire ligand-enriched mixture of sequences, are progressed from steps d) and e) to step f).

22. A method according to claim 1, wherein the ligand-enriched sequences having an aptameric potential falling in a mean or upper percentile range are progressed from steps d) and e) to step f).

23. A method according to claim 1, wherein the ligand-enriched sequences having a statistically insignificant aptameric potential are removed from the candidate pool.

24. A method according to claim 1, wherein non-binding candidate sequences are eluted and discarded from the candidate pool.

25. A method according to claim 1, wherein the method further comprises removing numerically dominant sequences from the candidate pool.

26. A method according to claim 1, wherein the method further comprises obtaining the full sequence of the candidate aptamers present in the final pool.

27. A method according to claim 1, wherein members of the ligand-enriched mixture of sequences having an aptameric potential of greater statistical significance as compared to the entire ligand-enriched mixture of sequences, or motifs derived from such sequences, are used to design new candidate aptamer pools.

28. A method according to claim 1, wherein members of the ligand-enriched mixture of sequences, and/or motifs thereof, having an aptameric potential of greater statistical significance, as compared to the entire ligand-enriched mixture of sequences, are used to influence random changes to and/or recombination of sequences showing a high aptameric potential.

29. A method according to claim 1, wherein the method further comprises modifying candidate sequences to increase stability and/or binding potential.

\* \* \* \* \*